US00PP28696P2

(12) United States Plant Patent
Ritchie et al.

(10) Patent No.: US PP28,696 P2
(45) Date of Patent: Nov. 28, 2017

(54) ***PITTOSPORUM* PLANT NAMED 'GLOBALL'**

(50) Latin Name: *Pittosporum tenuifolium*
Varietal Denomination: GloBall

(71) Applicants: John Stanley Ritchie, Otane (NZ); Kathleen Anne Ritchie, Otane (NZ)

(72) Inventors: John Stanley Ritchie, Otane (NZ); Kathleen Anne Ritchie, Otane (NZ)

( * ) Notice: Subject to any disclaimer, the term of this patent is extended or adjusted under 35 U.S.C. 154(b) by 0 days.

(21) Appl. No.: 15/330,696

(22) Filed: Oct. 28, 2016

(51) Int. Cl.
*A01H 5/00* (2006.01)

(52) U.S. Cl.
USPC ..... Plt./234

(58) Field of Classification Search
USPC ..... Plt./234, 226
CPC ..... A01H 5/00
See application file for complete search history.

*Primary Examiner* — Kent L Bell

(57) ABSTRACT

A new cultivar of *Pittosporum* plant named 'GloBall' that is characterized by a a spherical overall shape, a compact habit and variegated leaves that are green with irregular cream colored margins.

1 Drawing Sheet

Botanical classification: *Pittosporum tenuifolium.*
Variety denomination: 'GloBall'.

BACKGROUND OF THE INVENTION

The present invention relates to a new and distinct cultivar of *Pittosporum* plant botanically known as *Pittosporum tenuifolium* and hereinafter referred to by the cultivar name 'GloBall'.

The new cultivar was discovered by the inventor in a cultivated area of Otane, New Zealand in 2008. 'GloBall' was discovered as a naturally occurring branch mutation of *Pittosporum* 'Tiny Tyler' (not patented).

Asexual reproduction by cuttings of the new cultivar 'GloBall' was first performed in 2008 in Otane, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pittosporum* cultivar 'GloBall'.

1. *Pittosporum* 'GloBall' exhibits a spherical overall shape.
2. *Pittosporum* 'GloBall' exhibits a compact habit.
3. *Pittosporum* 'GloBall' exhibits variegated leaves that are green with irregular cream colored margins.

The closest comparison cultivars are the parent plant *Pittosporum* 'Tiny Tyler' and *Pittosporum* 'Golf Ball' (U.S. Plant Pat. No. 15,329). The new cultivar 'GloBall' is distinguishable from 'Tiny Tyler' by the following characteristics:

1. 'GloBall' exhibits a spherical overall shape and a compact habit. In comparison, 'Tiny Tyler' is more egg shaped and has a larger overall height.
2. 'GloBall' exhibits variegated leaves that are green with irregular cream colored margins. In comparison, the leaves of 'Tiny Tyler' are lighter green in color.

The new cultivar 'GloBall' is distinguishable from 'Golf Ball' by the following characteristics:

1. 'GloBall' exhibits variegated leaves that are green with irregular cream colored margins. In comparison, the leaves of 'Golf Ball' are not variegated and are darker green in color.
2. The leaves of 'GloBall' are larger than the leaves of 'Golf Ball'.

BRIEF DESCRIPTION OF THE DRAWING

The accompanying photograph illustrates the distinguishing traits of *Pittosporum* 'GloBall'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Pittosporum* cultivar named 'GloBall'. Data was collected in Otane, New Zealand from 12 month old outdoor grown plants in 2.5 liter containers. The time of year was Spring in the Southern Hemisphere and the average temperature range was 10 to 25 degrees Centigrade during the day and 5 to 12 degrees Centigrade at night. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'GloBall' has not been tested under all possible conditions and phenotypic differences may be observed with variations in environmental, climatic, and cultural conditions, however, without any variance in genotype.

Botanical classification: *Pittosporum tenuifolium* 'GloBall'.
Use: Ornamental perennial.
Parentage: 'GloBall' is a naturally occurring branch mutation of *Pittosporum* 'Tiny Tyler'.
Vigor: Moderate.
Growth rate: Fast.
Growth habit: Freely branching, dense, bushy habit.

Plant shape: Spherical, compact.
Suitable container size: 2.5 liter container.
Height: Average 100 cm. in height.
Width: Average 90 cm. in width.
Low temperature tolerance: −4 degrees Centigrade.
High temperature tolerance: 38 degrees Centigrade.
Propagation: Cuttings.
Time to initiate roots: Approximately 23 days in the Summer at 21 degrees Centigrade and 32 days in the Winter at 18 degrees Centigrade.
Time to produce a rooted cutting: Approximately 120 days in the Summer at 21 degrees Centigrade and 180 days in the Winter at 18 degrees Centigrade.
Root system: Fine and fibrous.
Lateral branches:
*Quantity*.—Approximately 26.
*Dimensions*.—Average 25.0 cm. in length and 3.25 mm. in diameter.
*Internode length*.—Average 16.0 mm.
*Stem color*.—200D.
*Stem pubescence*.—Absent.
*Stem texture*.—Glabrous.
*Stem luster*.—Dull.
*Strength*.—Moderate.
*Pinching*.—No.
Foliage:
*Leaf arrangement*.—Alternate.
*Leaf attachment*.—Petiolate.
*Compound or single*.—Single.
*Quantity of leaves per lateral branch*.—Approximately 18.
*Leaf shape*.—Elliptic.
*Leaf apex*.—Acute.
*Leaf base*.—Attenuate.
*Leaf length*.—Average 3.5 cm. in length.
*Leaf width*.—Average 1.5 cm. in width.
*Texture*.—Smooth (both surfaces).
*Luster*.—Glossy (both surfaces).
*Pubescence*.—Absent.
*Leaf margin*.—Entire, undulate.
*Vein pattern*.—Pinnate.
*Young leaf color* (*upper surface*).—146A, irregular margins 162C.
*Young leaf color* (*lower surface*).—148B, irregular margins 162C.
*Mature leaf color* (*upper surface*).—146A, irregular margins 162C.
*Mature leaf color* (*lower surface*).—146B, irregular margins 162C.
*Durability of foliage to stress*.—Moderate to high.
Petiole:
*Dimensions*.—Average 6.0 mm. in length and 1.2 mm. in diameter.
*Texture*.—Glabrous.
*Color*.—147C.
Flowers: *Pittosporum* 'GloBall' has not produced flowers to date.
Fruit and seed: *Pittosporum* 'GloBall' has not produced fruit or seed to date.
Disease and insect resistance: Plants of the new *Pittosporum* have not been observed for disease or insect resistance to date.

The invention claimed is:

1. A new and distinct variety of *Pittosporum* plant named 'GloBall' as described and illustrated.

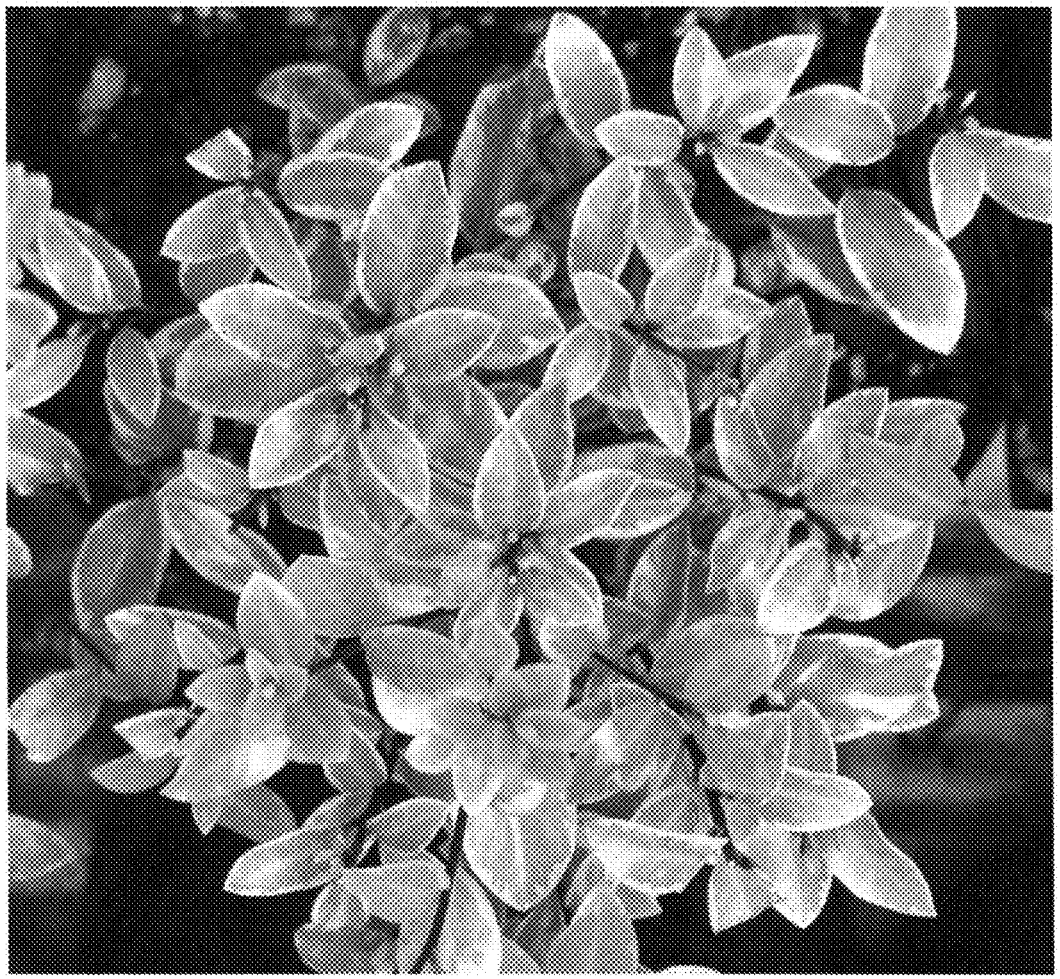

* * * * *